United States Patent [19]

Thorogood

[11] 4,396,771
[45] Aug. 2, 1983

[54] IMIDAZOLE DERIVATIVES AND SALTS THEREOF

[75] Inventor: Peter B. Thorogood, London, England

[73] Assignee: Burroughs Wellcome Co., Research Triangle Park, N.C.

[21] Appl. No.: 67,379

[22] Filed: Aug. 17, 1979

Related U.S. Application Data

[63] Continuation-in-part of Ser. No. 952,796, Oct. 19, 1978, abandoned, which is a continuation-in-part of Ser. No. 936,407, Aug. 24, 1978, abandoned.

[30] Foreign Application Priority Data

Oct. 19, 1977 [GB] United Kingdom ............... 43512/77
Aug. 8, 1978 [GB] United Kingdom ............... 32536/78
Aug. 22, 1978 [GB] United Kingdom ............... 34089/78
Nov. 27, 1978 [GB] United Kingdom ............... 46157/78

[51] Int. Cl.³ .................. C07D 233/58; C07D 233/60
[52] U.S. Cl. ............................... 548/335; 424/273 R; 542/457; 542/458; 542/470; 548/341
[58] Field of Search ....................... 548/342; 548/347; 548/373; 548/335; 542/457, 458, 470

[56] References Cited

U.S. PATENT DOCUMENTS

| | | | |
|---|---|---|---|
| 3,853,995 | 12/1974 | Wehrmeister | 542/458 X |
| 3,927,017 | 12/1975 | Heeres et al. | 548/335 |
| 4,006,243 | 2/1977 | Strehlke et al. | 424/273 |
| 4,036,975 | 7/1977 | Walker et al. | 424/273 R |
| 4,085,209 | 4/1978 | Miller et al. | 548/337 X |
| 4,110,447 | 8/1978 | Gante et al. | 548/335 X |
| 4,115,578 | 9/1978 | Miller et al. | 548/335 X |

FOREIGN PATENT DOCUMENTS 719664 8/1968 Belgium .

OTHER PUBLICATIONS

Iwasaki, S., *Helv. Chim. Acta,* 59(8), 2753–2764, (1976).
Iwasaki, S., *Helv. Chim. Acta,* 61(8), 2831–2842, (1978).
Moncada, S. et al., *Prostaglandins,* 13(4), 611–618, (1977).
Baggaley, K. et al., *J. Med. Chem.,* 18(8), 833–836, (1975).

*Primary Examiner*—Richard A. Schwartz
*Attorney, Agent, or Firm*—Donald Brown

[57] ABSTRACT

1-Substituted-imidazoles of the formula:

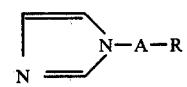

(I)

in which A is selected from the group consisting of straight or branched, saturated or unsaturated, acyclic hydrocarbon radicals of from 1 to 3 carbon atoms and R is

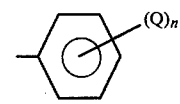

wherein n is an integer which is at least 1, and the or each Q substituent, which when n is greater than 1 may be the same or different, is selected from a saturated alkyl group of from 1 to 4 carbon atoms or an unsaturated alkyl group of from 2 to 4 carbon atoms, with the proviso that when A is unsaturated Q may also be selected from alkoxy of from 1 to 4 carbon atoms; halo; trihalomethyl; hydroxy; carboxyl; a salt of such a carboxyl group; carboalkyloxy; carboaryloxy; carboarylalkyloxy; —NR⁶R⁷ or —CONR⁶R⁷; in which R⁶ and R⁷ may be the same or different and are hydrogen or alkyl of from 1 to 4 carbon atoms; the 1-substituted-imidazole being the free base or an acid addition salt thereof.

Methods of preparing the 1-substituted-imidazoles are also provided.

The imidazoles have pharmacological properties that make them of use in the treatment of thromboembolic disorders, shock and angina pectoris.

17 Claims, No Drawings

IMIDAZOLE DERIVATIVES AND SALTS THEREOF

CROSS REFERENCE TO PRIOR APPLICATIONS

This application is a continuation-in-part of my Application Ser. No. 952 796, filed Oct. 19, 1978, now abandoned, which is in turn a continuation-in-part of my Application Ser. No. 936 407, filed Aug. 24, 1978, now abandoned.

The present invention relates to imidazole derivatives and salts thereof, to their synthesis and intermediates therefor, to pharmaceutical formulations containing such compounds and to the use of these compounds in medicine.

Thromboxane $A_2$ ($TXA_2$), a potent stimulator of blood platelet aggregation, is produced, in platelets, from the prostaglandin endoperoxides $PGG_2$ and $PGH_2$. Prostacyclin ($PGI_2$), which has potent anti-aggregatory activity, is also produced (in blood vessel walls) from $PGG_2$ and $PGH_2$, and it has been suggested that a balance between the production of $TXA_2$ and $PGI_2$ is the controlling factor in thrombus formation. It would, in consequence, be desirable in the treatment and prophylaxis of thrombo-embolic disorders to be able to selectively inhibit $TXA_2$ synthetase, and thereby favour the production of the anti-aggregatory agent $PGI_2$.

Imidazole and 1-methylimidazole are known to provide some degree of inhibition of the enzymic conversion of the endoperoxides ($PGG_2$ and $PGH_2$) to thromboxane $A_2$ by platelet microsomes (Moncada et al., Prostaglandins, 13/4, 611–618, 1977). Certain 1-n-alkylimidazoles, especially 1-n-dodecylimidazole and its higher homologues have been described as being capable of lowering serum cholesterol levels (U.K. Patent No. 1 364 312; Biochem. Pharmacol. 24, 1902–1903, 1975).

We have now discovered that $TXA_2$ synthetase may be inhibited by 1-substituted-imidazoles, e.g. 1-arylalkylimidazoles of formula (I) and acid addition salts thereof. Compounds of formula (I) and their salts are hereinafter referred to as the "active compounds".

The compounds of formula (I) are novel and of formula:

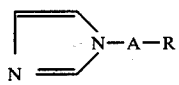

(I)

in which

A is selected from the group consisting of straight or branched, saturated acyclic hydrocarbon radicals of 1, 2 or 3 carbon atoms, and straight or branched, unsaturated acyclic hydrocarbon radicals of 2 or 3 carbon atoms, and R is

wherein n is an integer which is at least 1, and the or each Q substituent, which when n is greater than 1 may be the same or different, is a saturated hydrocarbon group of from 1 to 4 carbon atoms or an unsaturated hydrocarbon group of from 2 to 4 carbon atoms, with the provisos that (a) when A is a methylene or ethylidene group, n is at least 2 when each Q is a saturated hydrocarbon group;

(b) when A is a branched propylene, or straight propylidene group, n is at least 3 when each Q is a saturated hydrocarbon group; and (c) when the group A is unsaturated Q may also be selected from alkoxy of from 1 to 4 carbon atoms; alkylenedioxy of from 1 to 4 carbon atoms when n is at least 2; halo; trihalomethyl; hydroxy; carboxyl; a salt of such a carboxyl group; carboalkoxy; carboaryloxy; carboarylalkyloxy; $-NR^6R^7$ or $-CONR^6R^7$, in which $R^6$ and $R^7$ may be the same or different and are hydrogen or alkyl of from 1 to 4 carbon atoms, with the further proviso that when n is 1, Q is not a saturated hydrocarbon groups;

the substituted-imidazole being the free base or an acid addition salt thereof.

In formula (I) examples of the group A are:
methylene,
propylene, and,
in the orientation of formula (I), $-CH_2-CH=CH-$ (cis or trans or cis-trans isomeric mixture).

A valuable class of compounds of formula (I) are those in which the aromatic ring is substituted by at least two groups Q, preferably saturated or unsaturated hydrocarbon groups, e.g. alkyl or alkenyl groups, especially if one substituent is in the 4-position in the benzene ring and A is either methylene ($-CH_2-$), or, in the orientation of formula (I), $-CH_2-CH=CH$ (cis or trans- or cis-trans mixture-cinnamyl compound). When A is unsaturated, preferred compounds are those in which the aromatic ring contains alkyl, chloro or methoxy substituents.

Compounds of formula (I) may also be used as acid addition salts thereof, especially as pharmaceutically acceptable ones.

Especially preferred 1-arylalkyl compounds include:
1-(3,4-dimethylbenzyl)imidazole;
1-(2,4-dichlorocinnamyl)imidazole i.e. 1-(3-(2,4-dichlorophenyl)prop-2-enyl)imidazole;
1-(3-(2,6-dichlorophenyl)prop-2-enyl)imidazole;
1-(2,4,6-trimethylbenzyl)imidazole; and acid addition salts thereof.

Other preferred compounds include:
1-(3-(3,4,5-trimethoxyphenyl)prop-2-enyl)imidazole;
1-(3-(3,4-dimethoxyphenyl)prop-2-enyl)imidazole;
1-(3(2-hydroxyphenyl)prop-2-enyl)imidazole;
1-(3-(3-bromophenyl)prop-2-enyl)imidazole;
1-(3-(4-chlorophenyl)prop-2-enyl)imidazole;
1-(3-(3,4-dimethylphenyl)prop-2-enyl)imidazole;
1-(3-(2-methoxyphenyl)prop-2-enyl)imidazole; and acid addition salts thereof.

In contrast to imidazole and 1-methyl-imidazole the compounds of formula (I) are more potent inhibitors of $TXA_2$ synthetase. Many of the compounds (for example in (I) when A is $-CH_2-$ or, in the orientation of formula (I), $-CH_2-CH=CH-$) are also more selective in their action in not inhibiting other anti-aggregatory-prostaglandin generating enzymes. The compounds of formula (I) also do not produce the side-effects found with imidazole upon in vivo administration. The compounds of formula (I) are further capable of inhibiting platelet aggregation in vivo and also are capable of disaggregating platelet clumps, e.g. the compound 1-(3,4-dimethylbenzyl)imidazole and its salts especially displaying these properties.

The compounds of formula (I) are suitable for use in the treatment or prophylaxis of angina pectoris. In some cases it is possible to prevent the onset of agina pectoris, for example when a patient with coronary artery disease is given cardiac pacing, which leads generally to an increase of $TXA_2$ in the blood, and which is associated with the onset of angina pectoris. Also, inhibition of $TXA_2$ formation prevents or delays the onset of shock, e.g. experimentally induced shock in laboratory animals.

Imidazoles of formula (I) and acid addition salts thereof may be made by any method known in the art for the synthesis of compounds of analogous structure. In general these methods comprise linking the imidazole ring to the remainder of the molecule; converting a precursor molecule by elimination of a functional group from the imidazole ring; and formation of the desired compound from a corresponding pyrazole, imidazoline, or other unsaturated analogue.

A most convenient method of synthesis involves the reaction of imidazole (formula II) or a salt thereof with an alkylating or alkenylating agent of formula (III):

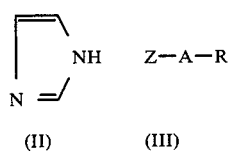

(II)        (III)

wherein R and A are as defined in formula (I) and Z is a leaving group. This reaction is well established in the literature, and the leaving group may be chosen from a variety of substituents but especially halo, preferably chloro or bromo, or from p-toluenesulphonyloxy but other arylsulphonyloxy, alkanesulphonyloxy or aralkylsulphonyloxy radicals may be used. The reaction is preferably performed in the presence of an acid acceptor, for example an alkali metal alkoxide such as sodium methoxide or potassium tertiary butoxide in the presence of an alkanol. The leaving group Z may itself be formed in situ from the corresponding alkanol (Z=OH) by reaction with a hydrohalogenic acid (e.g. hydrochloric acid or a Lewis acid, such as aluminium chloride: see Japanese Patent Kokai No. 131577/77) and the resulting agent of formula (III) reacted directly with imidazole without prior isolation. Alternatively an alkanol (Z=OH) or a derivative thereof (e.g. Z=R—A—O) may be reacted directly with imidazole (II) by heating in the presence of a dehydrating agent such as phosphoric acid, or a phosphate (see Japanese Patent Publication No. 51 105 060), sulphuric acid or sulphates (see Japanese Patent Publication No. 51 105 061).

Among precursor molecules which may be converted to a compound of formula (I) or an acid addition salt thereof, are substituted imidazole derivatives of formula (IV), or acid addition salts thereof

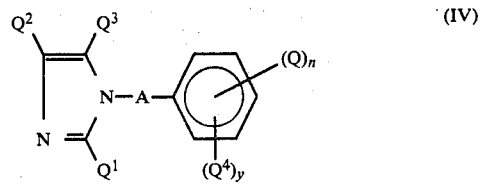

wherein A, n and Q are as defined in formula (I) and $Q^1$, $Q^2$, $Q^3$ and $Q^4$ are the same or different, at least one being a radical capable of removal by, for example, reduction or oxidation, the remaining radical or radicals being selected from hydrogen or a radical capable of removal in the same or another manner as the removable radical (e.g. a carboxyl group—see formula (VI)—removed by decarboxylation), y is 0 or an integer, with the proviso that y and n together do not exceed 5. $Q^1$, $Q^2$, $Q^3$ and $Q^4$ may be selected for example from thio (—SH), alkylthio (S-alkyl, wherein alkyl has from 1 to 4 carbon atoms) or halo, preferably chloro or bromo. The reaction conditions are chosen according to the nature of the radicals $Q^1$, $Q^2$, $Q^3$ and $Q^4$. Desulphurisation may be performed by oxidative or reductive procedures using for example nitric acid or Raney nickel; and reductive dehalogenation by the use of zinc and acetic acid or Raney nickel or other reagents known in the art or described in the literature.

Another class of examples include carboxyimidazoles or derivatives thereof of formula (VI):

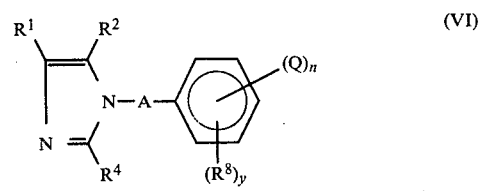

wherein A, n, Q, y and R are as defined in formula (IV), at least one of $R^1$, $R^2$, $R^4$ and $R^8$ is carboxyl or a derivative thereof (for example an ester such as an alkyl ester, an acid halide such as the chloride, or the nitrile) and the other is, or others are independently, hydrogen or carboxyl or a derivative as described. The compounds of formula (VI) may be converted into the imidazoles of formula (I) by any suitable decarboxylation conditions which may simply comprise heating the compounds with or without a catalyst such as copper.

The imidazoles of formula (I) may also be made from a compound of formula (VII):

wherein

is 1-imidazoline, 1-imidazole or 1-pyrazole, $A^1$ is a straight or branched saturated or unsaturated acyclic hydrocarbon radical which may include a keto group, and $R^3$ is

as defined in formula (I), or when A is unsaturated Q may be nitro, provided that at least one of

$A^1$ and $R^3$ is other than 1-imidazole, a saturated acyclic hydrocarbon and

respectively as defined in formula (I). Thus an imidazoline (VIII):

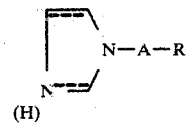

wherein one of --- represents an extra bond and, A and R are as defined in formula (I) may be dehydrogenated to the corresponding imidazole in the presence of a catalyst, for example by heating to 250° C. in the presence of palladium, nickel or platinum under pressure, or by heating with a dehydrogenating agent, such as selenium or copper oxide. 1-Pyrazole compounds (VII) may be treated with ultra-violet radiation, optionally under an inert atmosphere (e.g. argon) in for example 1,2-dimethoxyethane at room or elevated temperatures (see for example "Ring Transformations of Heterocycles" edited van der Plas, Academic Press, 1973 at page 261). The unsaturated imidazoles of formula (I) (in formula (VII), $A^1$ and/or Q (within $R^3$) are unsaturated) may be reduced to the corresponding less saturated or completely saturated compounds (but not reducing any aromatic nucleus) e.g. by hydrogenation with a noble metal catalyst, for example platinum or palladium in an alkanol. If Q is amino in the final product then its precursor may be a nitrogen-containing group reducible to amino, e.g. nitro. A compound of for example formula (IX);

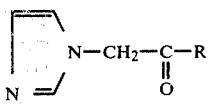

where R is as defined in formula (I), may be reduced at the keto group to a —$CH_2$— group for example by a Clemmensen reduction.

When one or more of the Q groups is an alkyl or alkenyl group it may be introduced into the phenyl ring by a Friedel Crafts or similar Lewis-acid catalysed reaction of the type

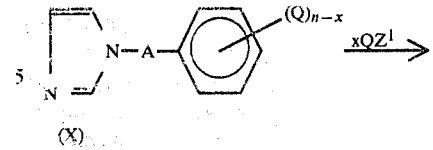

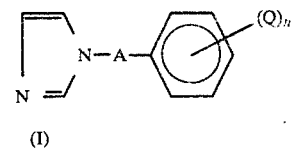

wherein A, Q and n are as defined for formula (I), x is an integer less than or equal to n and $Z^1$ is a leaving group, e.g. halo, suitable for use in this type of reaction.

Compounds of formula (I) may also be prepared by cyclising, preferably in the presence of an acid acceptor, a compound of formula (XI);

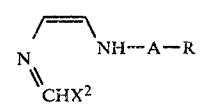

wherein A, R and n are as defined for formula (I) and $X^2$ is a leaving group.

Compounds of formula (I) may also be prepared by reacting a compound of formula (XII);

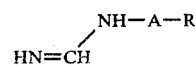

wherein A, R and n are as defined for formula (I) with a compound of formula (XIII);

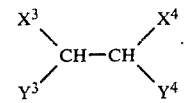

wherein either of $X^3$ and $Y^3$ is a leaving group such as halo or hydroxy and the other is hydrogen or $X^3$ and $Y^3$ are both halo or together with the carbon atom to which they are attached form an aldehyde group or an acetal derivative thereof e.g. both $X^3$ and $Y^3$ are alkoxy, and $X^4$ and $Y^4$ are as defined for $X^3$ and $Y^3$, although they may be the same as or different from $X^3$ and $Y^3$.

An imine salt of for example formula (XIIIa);

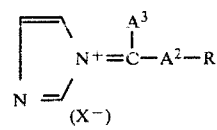

(wherein R is as defined for formula (I), $X^-$ is an anion, $A^2$ is a chemical bond or a straight or branching, saturated or unsaturated acyclic hydrocarbon radical, which may include a keto group, $A^3$ is hydrogen or a saturated or unsaturated acyclic hydrocarbon radical, which may include a keto group, with the proviso that $A^2$ and $A^3$ together contain no more than 2 carbon atoms), may be reduced to the corresponding compound of formula (I) by e.g. zinc and a mineral acid, e.g. hydrochloric acid.

The intermediates for use in the above-described reactions may also be made by conventional methods known in the art. Thus the 1-pyrazole and 1-imidazoline intermediates (formula (VII)) may be prepared by alkylation of pyrazole and imidazoline in an analogous manner to that described above for preparation of the corresponding imidazoles. The intermediates of formula (III) may be made in known manner preferably by halogenation of the corresponding alcohols (formula (III), Z=—OH). When A is unsaturated with three carbon atoms, the alcohol may be prepared from paraformaldehyde and the corresponding unsaturated A compound with two carbon atoms by analogy with the method described in Bull, Chem. Soc., Japan, 46/48, 25/2-5, (1973). The substituted imidazole intermediates of formula (IV) may be made in known manner, for example see "Imidazole and its derivatives" Part 1, Ed. K. Hoffmann, Interscience Publishers Inc. New York, 1973. For example the 2-thioimidazoles of formula (IV) may be made by cyclisation of an acetal of formula (XIV):

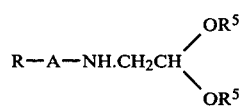

(XIV)

with thiocyanate, wherein $R^5$ is alkyl, aryl or arylalkyl.

The pharmaceutically acceptable acid addition salts of the compounds of formula (I) may be prepared by any method known in the art. In particular they may be prepared by treating the parent imidazole with the appropriate acid.

Examples of the acid addition salts of the compounds of formula (I) include those salts derived from the following acids: oxalic, hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic and benzenesulphonic.

The imidazoles of formula (I) may be used in conjunction with a phosphodiesterase inhibitor, which provides a further, synergistic, increase in effect, as it acts against platelet aggregation by a different pathway.

Suitable (cyclic AMP) phosphodiesterase inhibitors for use in potentiating the anti-aggregatory effects of the active compounds include as such or as pharmaceutically acceptable salts:

(a) Xanthine derivatives such as:
Theophylline(3,7-dihydro-1,3-dimethyl-1H-purine-2,6-dione), and salts thereof;
3-Isobutyl-1-methyl-xanthine;
Caffeine(3,7-dihydro-1,3,7-trimethyl-1H-purine-2,6-dione) and salts thereof; and
Aminophylline (adduct of Theophylline and 1,2-ethanediamine (2:1)).

(b) Isoquinoline derivatives, for example:
Papaverine(1-(3,4-dimethoxyhenyl)methyl-6,7-dimethoxyisoquinoline) and salts thereof; and
6,7-Diethoxy-1-(4,5-diethoxybenzyl)isoquinoline or its salts e.g. its hydrochloride;

(c) Derivatives of pyrimido(5,4-d)pyrimidine, for example:

Dipyridamole(2,2′,2″,2‴-(4,8-dipiperidinopyrimido[5,4-d]pyrimidin-2,6-diyl-dinitrilo)-tetraethanol) and its salts;
2,2′,2″,2‴-[[4-(1-piperidinyl)pyrimido[5,4-d]pyrimidin-2,6-diyl]dinitrilo]tetrakisethanol and its salts; and
2,4,6-tri-4-morpholinylpyrimido[5,4-d]pyrimidine and its salts.

(d) Derivatives of thieno[3,2-d]pyrimidine, for example:
N-[4-(4-morpholinyl)thieno[3,2-d]pyrimidin-2-yl]-1,2-ethanediamine.

(e) Derivatives of pyrazolo[3′,4′:2,3]pyrido[4,5-b][1,5]benzodiazepin-6-(3H)-one, for example:
3-Ethyl-7,12-dihydro-7,12-dimethyl-pyrazolo[4′,3′:5,6]pyrido[4,3-b]-[1,5]benzodiazepin-6-(3H)-one;
3-Ethyl-7,12-dihydro-9-methoxy-7,12-dimethyl-pyrazolo[3′,4′:2,3]pyrido[4,5-b][1,5]-benzodiazepin-6-(3H)-one; and
10-Chloro-3-ethyl-7,12-dimethyl-7,12-dihydropyrazolo[4′,3′:5,6]pyrido[4,3-b][1,5]benzodiazepin-6-(3H)-one.

(f) Derivatives of 1H- or 2H-pyrazolo[3,4-b]pyridine, for example:
4-(Butylamino)-1-ethyl-1H-pyrazolo[3,4-b]-pyridine-5-carboxylic acid ethyl ester;
4-(Butylamino)-1H-pyrazolo[3,4-b]pyridine-6-carboxylic acid ethyl ester;
4-Chloro-1-ethyl-3-methyl-1H-pyrazolo[3,4-b]pyridine-5-acetonitrile;
1-Ethyl-4-(isopropylidenehydrazino)-3-methyl-1H-pyrazolo[3,4-b]pyridine-5-carboxylic acid ethyl ester or its salt such as its hydrochloride hemihydrate; and
2-Methyl-6-phenyl-4-(1-piperidinyl)-2H-pyrazolo[3,4-b]pyridine or its salts e.g. its hydrochloride.

(g) Derivatives of 5H-furo-[3,4-e]pyrazolo[3,4-b]pyridine-5-one, for example:
4-(Butylamino)-1-ethyl-1,7-dihydro-7-hydroxy-5H-furo-[3,4-e]pyrazolo[3,4-b]pyridine-5-one; and (h) Derivatives of 1(2H)-naphthalenone, for example:
2[(Dimethylamino)methyl]-3,4-dihydro-7-methoxy-1(2H)-naphthalenone or its salts e.g. its 1:1 hydrochloride.

The active compounds are particularly useful in the treatment and/or prophylaxis of thrombo-embolic disorders in mammals, including man. It is to be understood that the term "thrombo-embolic disorder" includes those disorders whose etiology is associated with platelet aggregation.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts, cerebro-vascular thrombosis and ischaemic peripheral vascular disease; to treat and prevent post-operative thrombosis; and to promote patency of vascular grafts following surgery.

The active compounds are also useful as an addition to blood, blood products, blood substitutes and other fluids which are used in artificial extracorporeal circulation and perfusion of isolated body portions, e.g., limbs and organs, whether attached to the original body, detached and being preserved or prepared for transplant, or attached to a new body. It may also be used in laboratory animals, e.g. cats, dogs, rabbits, monkeys and rats, for these purposes in order to develop new methods and techniques for organ and limb transplants.

The active compounds also exhibit some vasodilatory action on blood vessels and therefore have a utility as anti-hypertensives for the treatment of high blood pressure in mammals, including man.

The active compounds may also be used in the preventing, treatment or prophylaxis of angina pectoris and in the prevention or delay of the onset of shock.

The amount of active compound required for therapeutic or prophylactic effect will vary with the route of administration, and the nature of the condition under treatment. In general a suitable dose for a mammal, including man, of active compound will lie in the range of 0.1 to 300 mg per kg body weight, particularly from 0.5 to 10 mg per kg body weight, for example 2 mg per kg. A suitable single oral dose for an adult human lies within the range of 50 to 600 mg, for example 150 mg, given say three times a day.

While it is possible for an active compound to be administered as the raw chemical it is preferable to present it as a pharmaceutical formulation. The formulations, both for veterinary and for human medical use, of the present invention comprise an active compound as above defined, together with one or more acceptable carriers therefor and optionally other therapeutic ingredients. The carrier(s) must be 'acceptable' in the sense of being compatible with the other ingredients of the formulation and not deleterious to the recipient thereof. Unit doses of a formulation may contain between 60 mg and 1.5 g of an active compound.

The formulations include those suitable for oral, rectal, vaginal or parenteral (including subcutaneous, intramuscular and intravenous) administration. Preferred formulations include tablets, capsules and injectable suspensions or solutions.

The formulations may conveniently be presented in unit dosage form and may be prepared by any of the methods well known in the art of pharmacy. All methods include the step of bringing into association the active compound (in the form of the base or a pharmaceutically acceptable acid addition salt) with the carrier which constitutes one or more accessory ingredients. In general the formulations are prepared by uniformly and intimately bringing into association the active compound with liquid carrier(s) or finely divided solid carrier(s) or both, and then, if necessary, shaping the product into the desired formulation.

It will be appreciated from the foregoing that the present invention provides the following features:-

(a) Novel 1-substituted imidazoles of formula (I) and acid addition salts thereof.

(b) Methods of preparing imidazoles of formula (I) and acid addition salts thereof.

(c) Pharmaceutical formulations containing an imidazole of formula (I) or a pharmaceutically acceptable acid addition salt thereof and a pharmaceutically acceptable carrier.

(d) Method of preparing the pharmaceutical formulations containing an imidazole of formula (I) or a pharmaceutically acceptable acid addition salt thereof.

(e) A method for the treatment or prophylaxis of a thrombo-embolic disorder in a mammal or mammalian tissue, including man or human tissue, comprising administering an effective amount of an active compound.

(f) A method of prevention, treatment or prophylaxis of angina pectoris in a mammal, including man, which comprises administering to the mammal, an effective amount of an imidazole of formula (I) or a pharmaceutically acceptable acid addition salt thereof.

(g) A method of preventing or delaying the onset of shock in a mammal which comprises administering to the mammal an effective amount of an imidazole of formula (I) or a pharmaceutically acceptable acid addition salt thereof.

The following Examples are provided by way of an illustration of the present invention and should in no way be construed as constituting a limitation thereof. All temperatures are given in degrees Celsius.

EXAMPLE 1

Preparation of 1-(3,4-Dimethylbenzyl)imidazole

1-Chloromethyl-3,4-dimethylbenzene (34.76 g, 0.225 mol) was added to a mixture of imidazole (13.6 g, 0.2 mol) and sodium bicarbonate (16.8 g, 0.2 mol) in dry methanol (100 ml). Following the addition, the reaction mixture was stirred and heated under reflux for 3 hours (h).

After cooling, the reactor mixture was filtered, and the filtrate was evaporated under reduced pressure to afford a yellow oil. The residue was extracted with chloroform (3×100 ml), and the combined extracts were washed with saturated brine (100 ml). The chloroform solution was dried over magnesium sulphate, and then concentrated under reduced pressure. The resulting oil was purified using a silica gel column and ethyl acetate/methanol (9:1) as eluent. The product fractions were pooled, concentrated, and the resulting oil was distilled to afford 1-(3,4-dimethylbenzyl)imidazole, b.p. 128°–130°/0.3 mm Hg.

EXAMPLE 2

Salts of 1-(3,4-Dimethylbenzyl)imidazole

A. Hydrogen Fumarate

A solution of fumaric acid (0.29 g, 0.0025 mol) in hot ethanol (10 ml) was added to a stirred solution of 1-(3,4-dimethylbenzyl)imidazole (0.46 g, 0.0025 mol) in hot ethanol (10 ml). After boiling for 0.25 h, the solution was evaporated to afford a white solid. Recrystallisation of the solid from ethyl acetate afforded 1-(3,4-dimethylbenzyl)imidazole hydrogen fumarate 1/6 hydrate as a white solid m.p. 138°–140°.

B. Hydrogen Succinate

A hot solution of succinic acid (0.295 g, 0.0025 mol) in ethanol (20 ml) was added to a stirred, hot solution of 1-(3,4-dimethylbenzyl)imidazole (0.46 g, 0.0025 mol) in hot ethanol (10 ml). After boiling for 0.25 h, the solution was evaporated under reduced pressure to afford a white solid. Recrystallisation of the solid from ethyl acetate/petroleum ether (b.p. 40°–60°) afforded 1-(3,4-dimethylbenzyl)imidazole hydrogen succinate as white crystals, m.p. 134°–135°

C. Hydrogen Oxalate

A hot solution of oxalic acid (0.225 g, 0.0025 mol) in dry ethanol (10 ml) was added to a solution of 1-(3,4-dimethylbenzyl)imidazole (0.46 g, 0.0025 mol) in hot ethanol (20 ml). After boiling for 0.25 h, the solution was evaporated to afford a white solid. Recrystallisation of the solid from ethanol/petroleum ether (b.p.

40°–60°) afforded 1-(3,4-dimethylbenzyl)imidazole hydrogen oxalate as a white solid, m.p. 92°–93°.

EXAMPLE 3

Preparation of
1-[3-(2,4-Dichlorophenyl)prop-2-enyl]imidazole

1-Chloro-3-(2,4-dichlorophenyl)prop-2-ene (11.1 g, 0.05 mol) was added dropwise to a stirrer solution of imidazole (3.4 g, 0.05 mol) and potassium tert-butoxide (5.6 g, 0.05 mol) in butan-1-ol (100 ml). Following the addition, the reaction mixture was stirred and heated under reflux for 3.5 h.

After cooling, the reaction mixture was filtered, and the filtrate was concentrated under reduced pressure. Hydrochloric acid (150 ml, 2 M) was then added to the residue and the aqueous mixture was washed with ether (1×60 ml). The acidic solution was then basified with sodium hydroxide solution (10 M), and the resulting oil was extracted with chloroform. The chloroform extracts were combined and dried over magnesium sulphate. Evaporation of the chloroform under reduced pressure afforded a pale yellow oil which was purified using a silica gel column and by elution with ethyl acetate/methanol (9:1). The product fractions were pooled and concentrated to afford an oil which was distilled, to afford 1-[3-(2,4-dichlorophenyl)prop-2-enyl]imidazole, b.p. 144°–148°/0.007 mmHg.

EXAMPLE 4

Preparation of
1-[3-(2,6-Dichlorophenyl)prop-2-enyl]imidazole

1-Chloro-3-(2,6-dichlorophenyl)prop-2-ene (11.1 g, 0.05 mol) was added dropwise to a stirred solution of imidazole (3.4 g, 0.05 mol) and potassium tert-butoxide (5.6 g, 0.05 mol) in butan-1-ol (100 ml). Following the addition, the reaction mixture was stirred and heated under reflux for 3.5 h.

After cooling, the reaction mixture was filtered, and the filtrate was concentrated under reduced pressure. Hydrochloric acid (150 ml, 2 M) was then added to the residue, and the aqueous mixture was washed with ether (1×60 ml). The acidic solution was then basified with sodium hydroxide solution (10 M), and the resulting oil was extracted with chloroform. The chloroform extracts were combined and dried over magnesium sulphate. Evaporation of the chloroform under reduced pressure afforded a pale yellow oil which was purified using a silica gel column and by elution with ethyl acetate/methanol (9:1). The product fractions were pooled and concentrated to afford an oil which was distilled, to afford 1-[3-(2,6-dichlorophenyl)prop-2-enyl]imidazole, b.p. 156°–158°/0.02 mmHg.

EXAMPLE 5

By the method described in Example 1 above the following compounds were prepared:
- (a) 1-(2,4,6-trimethylbenzyl)imidazol; B.p. 104°–108°/0.005 mm Hg;
- (b) 1-(3-(3,4,5-trimethoxyphenyl)prop-2-enyl)imidazole;
- (c) 1-(3-(3,4-dimethoxyphenyl)prop-2-enyl)imidazole;
- (d) 1-(3-(2-hydroxyphenyl)prop-2-enyl)imidazole;
- (e) 1-(3-(3-bromophenyl)prop-2-enyl)imidazole;
- (f) 1-(3-(4-chlorophenyl)prop-2-enyl)imidazole;
- (g) 1-(3-(3,4-dimethylphenyl)prop-2-enyl)imidazole;
- (h) 1-(3-(2-methoxyphenyl)prop-2-enyl)imidazole.

EXAMPLE 6

Biological Results horse platelets were prepared from whole horse blood by differential centrifugation. Approximately $10^6$ platelets were homogenised in 1 ml 100 mM Tris buffer pH 7.4. Various concentrations of active compound were added and the reaction sets incubated for 5 minutes at ambient temperature. To each tube was added 20 nM of arachidonic acid contaning $10^6$ DPM of labelled arachidonic acid and the tubes incubated for 3 minutes at 37° C. in a shaking water bath. After incubation the radioactive products were extracted from the acidified aqueous phase with ethyl acetate and after concentration resolved by thin layer chromatography on silica gel with chloroform/methanol/acetic acid/water (90:8:1:0.8) as a developing solvent. The amount of thromboxane produced was measured by scraping the radioactive zone corresponding to thromboxane $B_2$ and estimating the radioactivity in a liquid scintillation counter.

The concentration of active compound to reduce the enzyme activity by 50% ($ED_{50}$) was established. Thr results are shown in Table A.

The selectivity of the active compounds was measured in a similar manner to that described above and the amount of PGE, PGF and PGD produced was determined. The greater the selectivity, the more of the anti-aggregating prostaglandins are produced. The $ED_{50}$ and Selectivity results are shown in Table A in which 0 indicates no selectivity; + low selectivity and ++ medium selectivity.

TABLE A

| Compound | $ED_{50}$ μg/ml | Selectivity |
|---|---|---|
| 1-(3,4-Dimethylbenzyl)imidazole | 6 | ++ |
| 1-(3-(2,4-Dichlorophenyl)prop-2-enyl)imidazole | 4.1 | + |
| 1-(3-(2,6-Dichlorophenyl)prop-2-enyl)imidazole | 1 | + |
| 1-(2,4,6-Trimethylbenzyl)imidazole | 3.4 | ++ |

EXAMPLE 7

| | |
|---|---|
| 1-(3,4-Dimethylbenzyl)imidazole (as a salt) | 150 mg |
| Starch | 25 mg |
| Polyvinylpyrrolidone | 2 mg |
| Magnesium stearate | 3 mg |

The imidazole salt is ground to a fine powder blended with the starch and then the mixture granulated with an aqueous solution of the polyvinylpyrrolidone. The granules are sieved 1000μ, dried, sieved again and the magnesium stearate added. The mixture is then compressed into tablets.

In the same manner, tablets of 1-(3-(2,4-dichlorophenyl)prop-2-enyl)imidazole and 1-(3-(2,6-dichlorophenyl)prop-2-enyl)imidazole are prepared.

EXAMPLE 8

| Tablets formulation |  |
|---|---|
| Tablets (150 mg) of the imidazoles described in the preceding Example 7 are prepared in the same manner from the following ingredients: | |
| The imidazole compound (as a salt) | 150 mg |
| Lactose | 100 mg |
| Starch | 30 mg |
| Polyvinylpyrrolidone | 2 mg |

-continued

Tablets formulation
Tablets (150 mg) of the imidazoles described in
the preceding Example 7 are prepared in the same
manner from the following ingredients:

| | |
|---|---|
| Magnesium stearate | 3 mg |

In the preparation, the lactose is blended with the starch.

EXAMPLE 9

Tablet formulation
Tablets (100 mg) of the imidazoles of Example 7
are prepared in the same manner from the following
ingredients:

| | |
|---|---|
| The Imidazole Compound (as a salt) | 100 mg |
| Sodium starch glycollate | 10 mg |
| Polyvinylpyrrolidone | 2 mg |
| Magnesium stearate | 3 mg |

EXAMPLE 10

Tablet formulation
Tablets (150 mg) of the imidazoles of Example 7
are prepared in the same manner from the following
ingredients, except that the starch, pregelled starch
and imidazole compound are all blended together prior
to granulation:

| | |
|---|---|
| The Imidazole Compound (as a salt) | 150 mg |
| Starch | 25 mg |
| Pregelled starch | 5 mg |
| Magnesium stearate | 3 mg |

EXAMPLE 11

Injectable formulation

| | |
|---|---|
| Imidazole Compound of formula (I) | 15.0 g |
| Lactic Acid B.P. | q.s. to pH 3.0 |
| Water for Injections B.P. | to 100.0 ml |

Suspend the compound in ¾ of the available quantity of water. Add sufficient lactic acid to dissolve the compound and to reduce the pH to 3.0. Dilute to volume with Water for Injections.

Sterilise the solution by passage through a membrane filter, pore size 0.22 μm.

Distribute the solution using aseptic precautions into sterilised ampoules, 1 ml per ampoule. Seal by fusion of the glass.

Each 1 ml ampoule supplies 150 mg of the imidazole compound: 1(3,4-dimethylbenzyl)imidazole hydrogen fumarate.

EXAMPLE 12

Injectable formulation

| | |
|---|---|
| Imidazole Compound of formula (I) | 15.0 g |
| Citric Acid B.P. | q.s. to pH 3.0 |
| Chlorocresol | 0.1 g |
| Water for Injections to | 100.0 ml |

Suspend the compound in ½ the final volume of Water for Injections. Add sufficient citric acid as a 10% solution in Water for Injections to dissolve the compound and reduce the pH to 3.0. Dilute to volume with Water for Injections.

Sterilise the solution by passage through a membrane filter, pore size 0.22 μm.

Distribute the solution with aseptic precautions into sterilised vials, 25 ml per vial. Stopper with sterile rubber closures and seal with an aluminium cap.

Each 1 ml of solution provides 150 mg of the compound: 1-(3,4-dimethylbenzyl)imidazole hydrogen fumarate.

EXAMPLE 13

Injectable formulation

In the manner described in the preceding two Examples, injectable formulations of 1-(3-(2,4-dichlorophenyl)prop-2-enyl)imidazole and 1-(3-(2,6-dichlorophenyl)prop-2-enyl)imidazole salts were prepared.

I claim:

1. A 1-substituted-imidazole of the formula

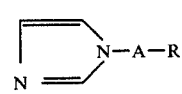 (I)

in which

A is selected from the group consisting of straight or branched, saturated, acyclic hydrocarbon radicals of 1, 2 or 3 carbon atoms, and straight or branched unsaturated acyclic hydrocarbon radicals of 2 or 3 carbon atoms, and R is

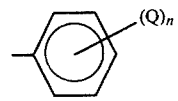

wherein n is an integer which is at least 1, and the or each Q substituent, which when n is greater than 1 may be the same or different, is selected from a saturated hydrocarbon group of from 1 to 4 carbon atoms and an unsaturated hydrocarbon group of from 2 to 4 carbon atoms, with the provisos that
(a) when A is ethylidene, n is at least 2 when each Q is a saturated hydrocarbon group;
(b) when A is straight propylidene, n is at least 3 when each Q is a saturated hydrocarbon group;
(c) when A is unsaturated Q may also be selected from alkoxy of from 1 to 4 carbon atoms; halo; trihalomethyl; hydroxy; carboxyl; a salt of such carboxyl group; carboalkoxy; carbophenoxy; carbophenalkyloxy; —NR⁶R⁷ or —CONR⁶R⁷; in which R⁶ and R⁷ may be the same or different and are hydrogen or alkyl of from 1 to 4 carbon atoms, with the further proviso that when n is 1, Q is not a saturated alkyl group nor halo;
(d) when A is methylene, ethylene or straight propylene, n is at least 3 when each Q is selected from a saturated hydrocarbon group; and
(e) when A is branched propylene, n is at least 4 when each Q is selected from a saturated hydrocarbon group;

the substituted-imidazole being the free base or a pharmaceutically acceptable acid addition salt thereof.

2. A compound according to claim 1 wherein n is at least 2.

3. A compound according to claim 2 wherein one of the groups is in the 4-position of the benzene ring, relative to the group A.

4. A compound according to claim 1 wherein A is —CH$_2$—.

5. A compound according to claim 1 wherein A is, in the orientation of formula (I), —CH$_2$—CH=CH—.

6. A compound according to claim 5 wherein the group Q is selected from alkyl, chloro or methoxy.

7. A 1-substituted-imidazole of the formula:

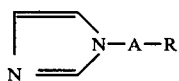
(I)

in which

A is selected from the group consisting of straight or branched, saturated, acyclic hydrocarbon radicals of 2 carbon atoms, and straight or branched unsaturated acyclic hydrocarbon radicals of 2 or 3 carbon atoms, and R Is

wherein n is an integer which is at least 1, and the or each Q substituent, which when n is greater than 1 may be the same or different, is selected from a saturated hydrocarbon group of from 1 to 4 carbon atoms and an unsaturated hydrocarbon group of from 2 to 4 carbon atoms, with the provisos that (a) when A is ethylidene, n is at least 2 when each Q is a saturated hydrocarbon group;

(b) when A is unsaturated Q may also be selected from alkoxy of from 1 to 4 carbon atoms; trihalomethyl; hydroxy; carboxyl; a salt of such a carboxyl group; carboalkoxy; —NR$^6$R$^7$ or —CONR$^6$R$^7$; in which R$^6$ and R$^7$ may be the same or different and are hydrogen or alkyl of from 1 to 4 carbon atoms, with the further proviso that when n is 1, Q is not a saturated alkyl group; and (c) when A is ethylene, n is at least 3 when each Q is a saturated hydrocarbon group; the substituted-imidazole being the free base or a pharmaceutically acceptable acid addition salt thereof.

8. A compound according to claim 7 wherein n is at least 2.

9. A compound according to claim 8 wherein one of the groups is in the 4-position of the benzene ring, relative to the group A.

10. 1-(3,4-dimethylbenzyl)imidazole or a pharmaceutically acceptable acid addition salt thereof.

11. 1-(3,4-dimethylbenzyl)imidazole.

12. A 1-substituted-imidazole selected from 1-[3-(2,4-dichlorophenyl)prop-2-enyl]imidazole, 1-[3-(2,6-dichlorophenyl)prop-2-enyl]imidazole and pharmaceutically acceptable acid addition salts thereof.

13. A 1-substituted imidazole selected from 1-(2,4,6-trimethylbenzyl)imidazole, 1-[3-(3,4-dimethylphenyl)-prop-2-enyl]imidazole and pharmaceutically acceptable acid addition salts thereof.

14. A 1-substituted-imidazole selected from the group consisting of:
1-[3-(3,4,5-trimethoxyphenyl)prop-2-enyl]imidazole;
1-[3-(3,4-dimethoxyphenyl)prop-2-enyl]imidazole;
1-[3-(2-hydroxyphenyl)prop-2-enyl]imidazole;
1-[3-(3-bromophenyl)prop-2-enyl]imidazole;
1-[3-(4-chlorophenyl)prop-2-enyl]imidazole;
1-[3-(2-methoxyphenyl)prop-2-enyl]imidazole; and pharmaceutically acceptable acid addition salts thereof.

15. 1-(2,4,6-Trimethylbenzyl)imidazole, or a pharmaceutically acceptable acid addition salt thereof.

16. A 1-substituted-imidazole of the formula:

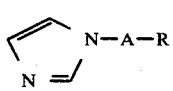
(I)

in which

A is a straight or branched unsaturated acyclic hydrocarbon radical of 2 or 3 carbon atoms, and R is

wherein n is an integer which is at least 1, and the Q substituent is selected from alkoxy of from 1 to 4 carbon atoms; trihalomethyl; hydroxy; carboxyl; a salt of such a carboxyl group; carboalkoxy; —NR$^6$R$^7$ or —CONR$^6$R$^7$; in which R$^6$ and R$^7$ may be the same or different and are hydrogen or alkyl of from 1 to 4 carbon atoms, the substituted-imidazole being the free base or a pharmaceutically acceptable acid addition salt thereof.

17. A compound according to claim 16 wherein A is, in the orientation of formula (I), —CH$_2$—CH=CH—.

* * * * *